United States Patent
McFadden

(10) Patent No.: US 9,829,019 B2
(45) Date of Patent: Nov. 28, 2017

(54) SWIVELING TAPER LOCK CONNECTOR

(71) Applicant: Joseph T McFadden, Norfolk, VA (US)

(72) Inventor: Joseph T McFadden, Norfolk, VA (US)

(*) Notice: Subject to any disclaimer, the term of this patent is extended or adjusted under 35 U.S.C. 154(b) by 0 days.

(21) Appl. No.: 15/475,966

(22) Filed: Mar. 31, 2017

(65) Prior Publication Data

US 2017/0284436 A1    Oct. 5, 2017

Related U.S. Application Data

(60) Provisional application No. 62/318,278, filed on Apr. 5, 2016.

(51) Int. Cl.
  *F16B 5/02*    (2006.01)
  *F16B 39/02*   (2006.01)

(52) U.S. Cl.
  CPC .......... *F16B 5/0225* (2013.01); *F16B 39/02* (2013.01)

(58) Field of Classification Search
  CPC .............. F16B 7/0433; Y10T 403/595; Y10T 403/7071; Y10T 403/7105; Y10T 403/7129; Y10T 403/7141; Y10T 403/7171; Y10T 403/7194; A61G 13/101
  See application file for complete search history.

(56) References Cited

U.S. PATENT DOCUMENTS

| | | | | |
|---|---|---|---|---|
| 5,792,046 A | * | 8/1998 | Dobrovolny | A61B 17/02 403/374.1 |
| 5,897,087 A | * | 4/1999 | Farley | A61B 17/02 248/229.21 |
| 6,033,363 A | * | 3/2000 | Farley | A61B 17/02 600/234 |
| 2008/0247818 A1 | * | 10/2008 | Oesch | A61B 17/645 403/389 |

FOREIGN PATENT DOCUMENTS

EP    0 992 227    * 4/2000 ............. A61G 13/10

* cited by examiner

Primary Examiner — Michael P Ferguson
(74) Attorney, Agent, or Firm — Peter J. Van Bergen

(57) ABSTRACT

A connector includes a first housing having a bore hole terminating in a machine taper tunnel, a tapered hole, and a slot extending through the first housing across its bore hole to its tapered hole. Similarly, a second housing has a bore hole, a tapered hole, and a slot extending through the second housing across its bore hole to its tapered hole. A rod disposed in the first and second housings' bore holes extends across the slots. The rod terminates at first and second ends with the second end being coupled to the second housing. The rod has a machine taper coupled thereto between its first and second ends for engagement with the machine taper tunnel. A lever, pivotally coupled to the rod's first end, can simultaneously cause the rod's machine taper to move relative to the machine taper tunnel and cause the width of the slots to change.

15 Claims, 3 Drawing Sheets

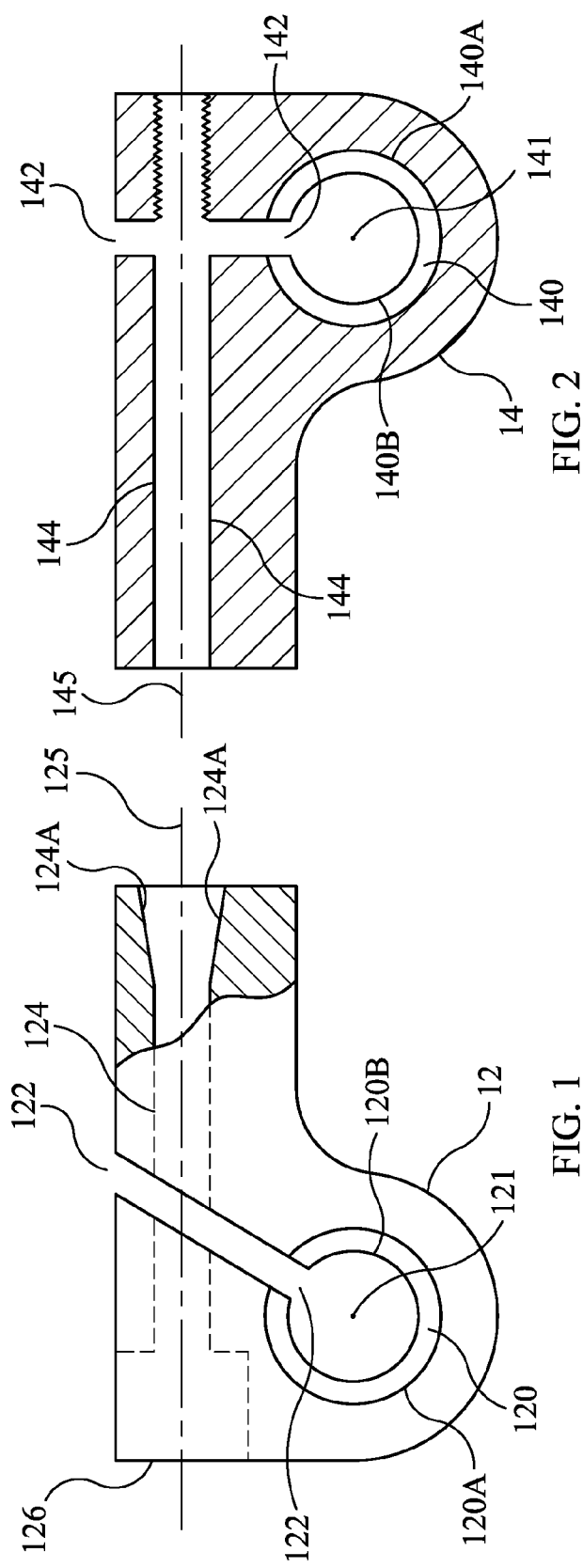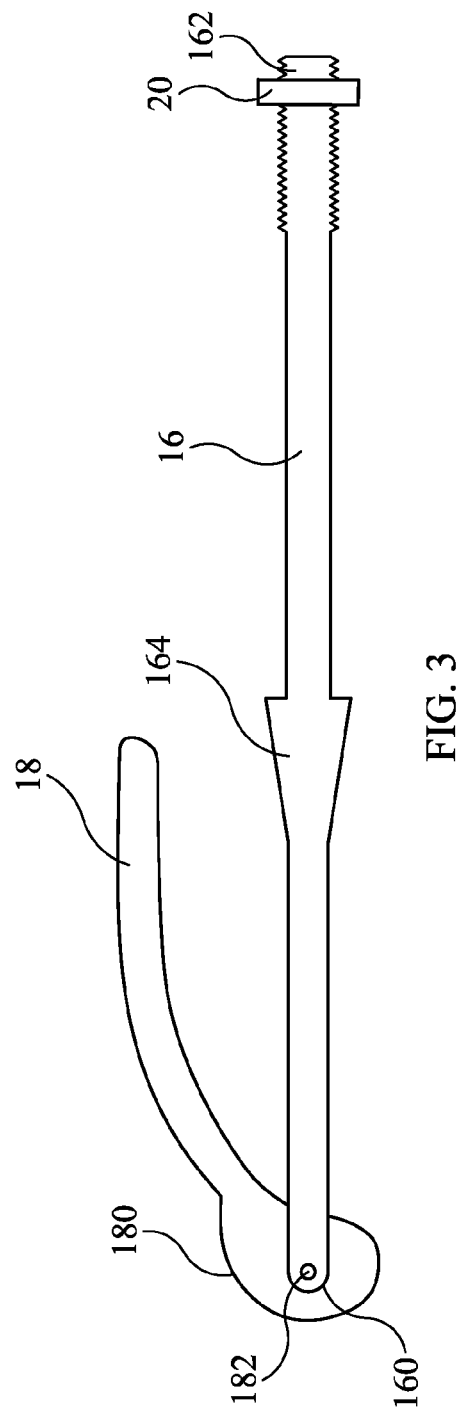

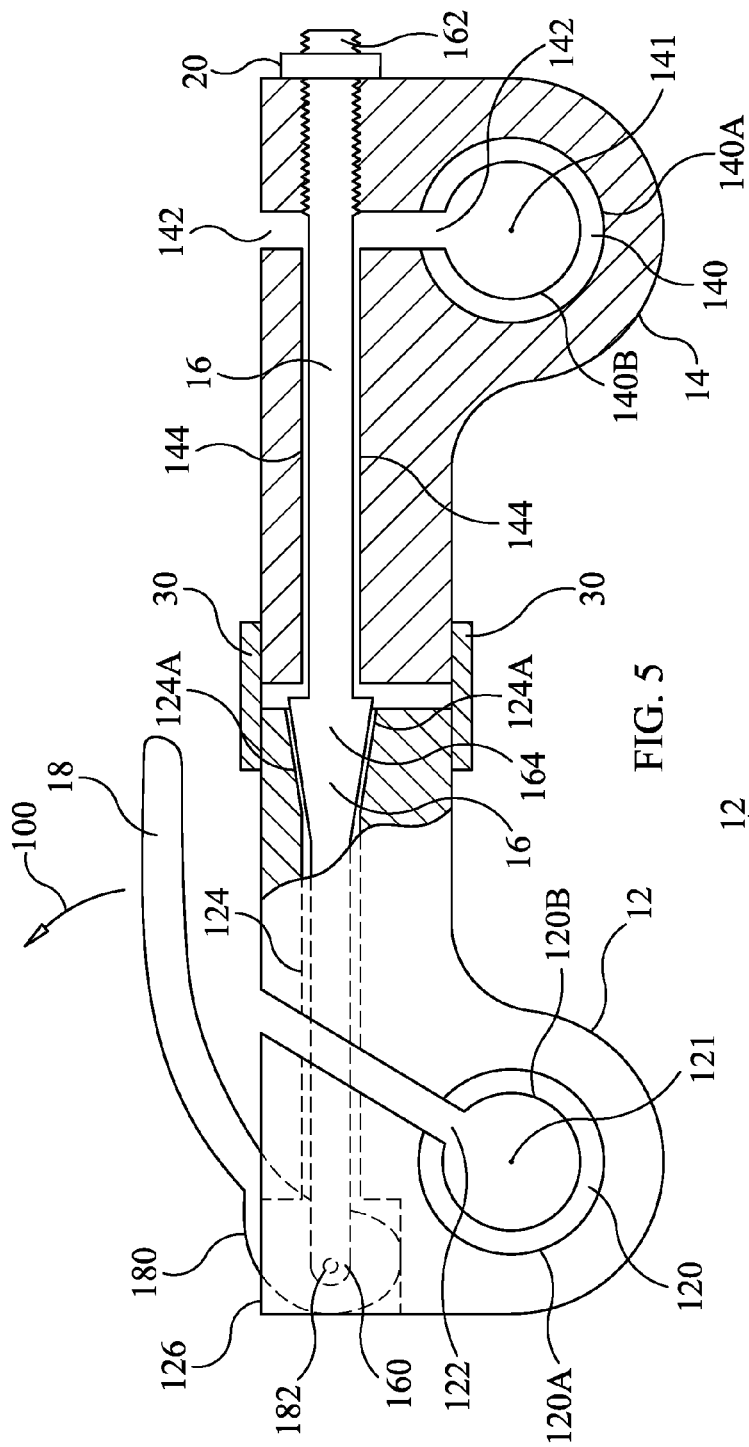
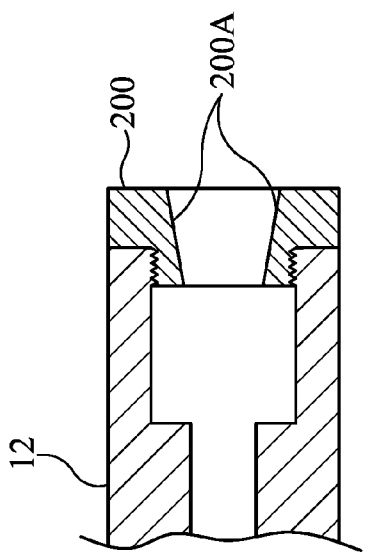
FIG. 5
FIG. 6

US 9,829,019 B2

SWIVELING TAPER LOCK CONNECTOR

Pursuant to 35 U.S.C. §119, the benefit of priority from provisional application 62/318,278, with a filing date of Apr. 5, 2016, is claimed for this non-provisional application.

FIELD OF THE INVENTION

The invention relates generally to connectors, and more particularly to a swiveling connector that can swivel to achieve a variety of positions and then have its connection and swivel points locked simultaneously.

BACKGROUND OF THE INVENTION

Clamps and clamping systems are used in a wide variety of applications to position and hold a workpiece. Such devices and systems must provide a high degree of positioning options and precision for certain applications. For example, during precision surgical operations such as neurosurgery, a patient's head must be properly positioned and then securely restrained once positioned. Towards this end, a variety of head clamps and head clamp positioning systems have been developed. While conventional head clamps utilize various positioning systems to include movable connectors that function adequately, there is room for improvement in terms of precision positioning, simplicity of achieving such precision positioning, and simplicity of retaining a precision position so-achieved.

SUMMARY OF THE INVENTION

Accordingly, it is an object of the present invention to provide a movable and lockable connector.

Another object of the present invention is to provide a connector that can swivel and have its swivel and connection points locked/unlocked simultaneously.

Other objects and advantages of the present invention will become more obvious hereinafter in the specification and drawings.

In accordance with the present invention, a connector includes a first housing having a first bore hole extending through the first housing and terminating in a machine taper tunnel, a first tapered hole extending through the first housing, and a first slot extending through the first housing across the first bore hole to the first tapered hole. The connector also includes a second housing having a second bore hole extending through the second housing, a second tapered hole extending through the second housing, and a second slot extending through the second housing across the second bore hole to the second tapered hole. A rod is disposed in the first bore hole and the second bore hole. The rod extends across the first slot and the second slot. The rod terminates at a first end and a second end with the second end being coupled to the second housing. The rod has a machine taper coupled thereto between the first end and the second end for engagement with the machine taper tunnel. A lever is pivotally coupled to the first end of the rod such that a pivoting movement of the lever causes the machine taper to move relative to the machine taper tunnel.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 1 is an isolated part side view and a part cross-sectional view of the first housing used in a swiveling taper lock connector in accordance with an embodiment of the present invention;

FIG. 2 is an isolated cross-sectional view of a second housing used in a swiveling taper lock connector in accordance with an embodiment of the present invention;

FIG. 3 is an isolated side view of a rod and locking/release handle used a swiveling taper lock connector in accordance with an embodiment of the present invention;

FIG. 5 is a part side view and a part cross-sectional view of a fully assembled swiveling taper lock connector in accordance with another embodiment of the present invention; and FIG. 6 is an isolated cross-sectional view of one end of the first housing illustrating an attachable Machine taper tunnel region in accordance with another embodiment of the present invention.

DETAILED DESCRIPTION OF THE INVENTION

Figure 4:
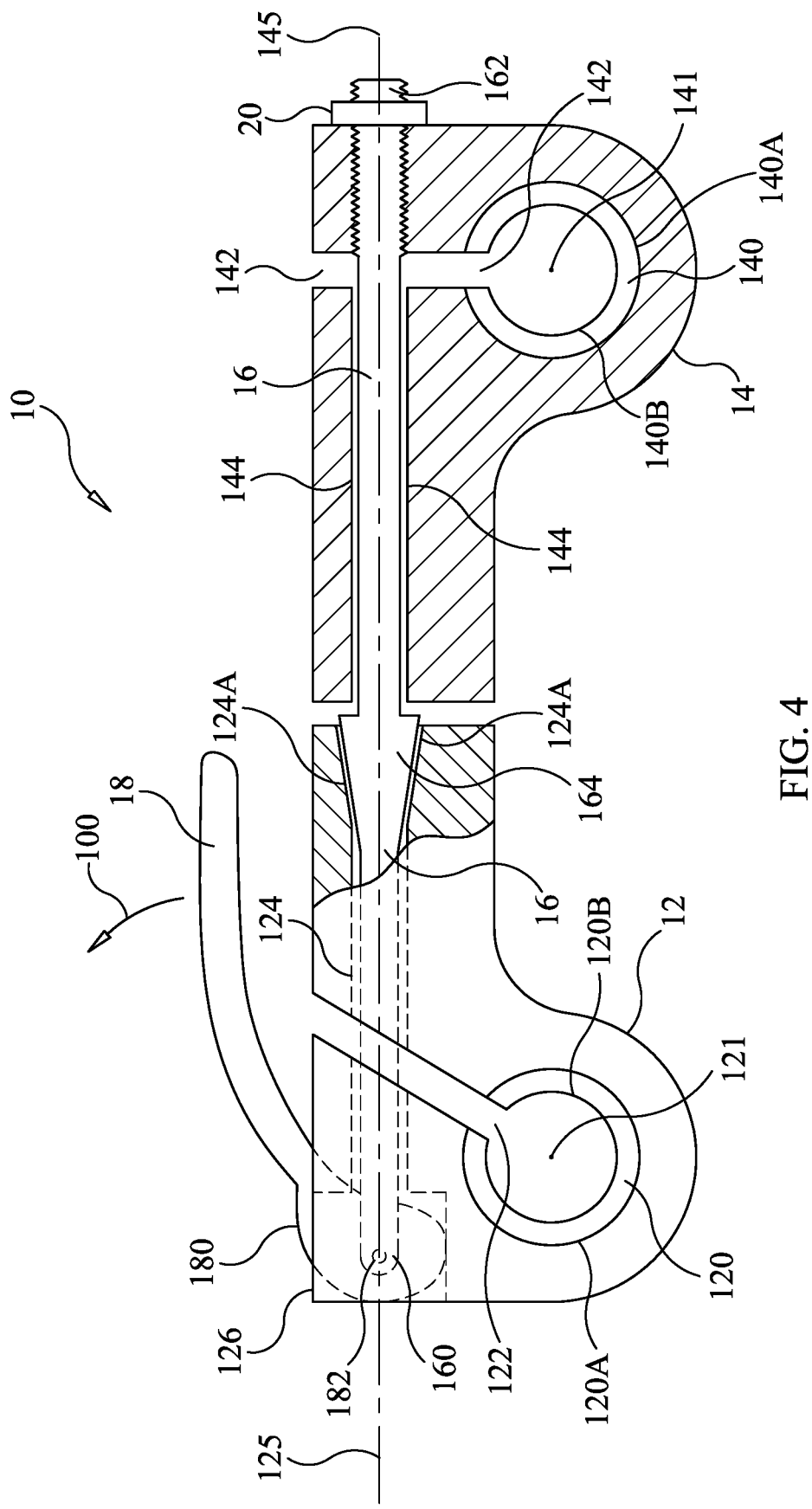
FIG. 4 is a part side view and a part cross-sectional view of a fully assembled swiveling taper lock connector in accordance with an embodiment of the present invention.

Referring now to the drawings, simultaneous reference will be made to FIGS. 1-4 where FIGS. 1-3 are isolated views of components of a swiveling taper lock connector in accordance with an embodiment of the present invention that is shown fully assembled in FIG. 4 where the fully assembled connector is referenced generally by numeral 10. The present invention can be used in a variety of applications without departing from the scope of the present invention. For example, connector 10 can be used in the positioning and retention of a surgical head clamp (not shown) relative to a mounting "frame" that is typically part of (or coupled to) a surgical operating table (not shown). However, it is to be understood that the present invention is not so limited as it can also be used as a swiveling connector in a variety of other applications.

In general, connector 10 includes a two-piece housing and a connecting rod. The two-piece housing includes a first housing piece designated by reference numeral 12 (hereinafter referred to simply as "housing 12") and a second housing piece designated by reference numeral 14 (hereinafter referred to simply as "housing 14"). Both housing 12 and housing 14 are generally made from a rigid material (e.g., metal, composite, plastic, etc.), the choice of which can be selected based on the needs of the particular application. As will be explained further below, the connecting rod (referenced by numeral 16) passes through housing 12 and housing 14 to hold them together when housings 12/14 are (i) allowed to swivel 360° relative to one another about rod 16, and (ii) locked to prevent such swiveling motion while simultaneously locking onto two taper rods/pins (not shown). In general, rod 16 is rigidly coupled to a portion of housing 14, but is movable within housing 12 as will be explained further below.

Housing 12 defines a slotted and tapered ("S/T") tunnel region 120 with a slot 122 extending along the length of S/T tunnel region 120. Slot 122 also continuously extends from S/T tunnel region 120 through housing 12 such that slot 122 extends across a bore hole 124 that receives a portion of rod 16 there through. S/T tunnel region 120 has a larger diameter at one end 120A than at its other end 120B with the walls of S/T tunnel region 120 being tapered between ends 120A and 12B. The longitudinal axis 121 of S/T tunnel region 120 is approximately perpendicular to the longitudinal axis 125 of bore 124. In general, bore hole 124 allows rod 16 to slide axially therein while also allowing housing 12 to swivel about the longitudinal axis of rod 16. For reasons that will be explained further below, bore hole 124 defines a self-holding machine taper tunnel region (as indicated by reference numeral 124A) where housing 12 is adjacent to housing 14 (FIG. 4). A variety of self-holding machine taper designs can be used in the present invention without departing from the scope of the present invention. By way of example, machine taper tunnel region 124A can be a Jacobs taper tunnel region. Housing 12 also has an end 126 that supports one outboard end 160 of rod 16. A lock/release handle or lever 18 includes a cam end 180 positioned at end 126 and pivotally coupled to outboard end 160 as indicated by reference numeral 182.

Housing 14 also defines a slotted and tapered ("S/T") tunnel region 140 with a slot 142 extending along the length of S/T tunnel region 140. Slot 142 also continuously extends from S/T tunnel region 140 through housing 14 such that slot 142 extends across a bore hole 144 that receives a portion of rod 16 passing there through. S/T tunnel region 140 has a larger diameter at one end 140A than at its other end 140B with the walls of S/T tunnel region 140 being tapered between ends 140A and 140B. The longitudinal axis 141 of S/T tunnel region 140 is approximately perpendicular to the longitudinal axis 145 of bore hole 144. In general, rod 16 can move axially within bore 144 that is inboard of slot 142, but rod 16 is rigidly coupled to housing 14 at a portion thereof that is outboard of slot 142. For example, bore hole 144 can have threaded walls after slot 142 (i.e., at the outboard end of housing 14 as shown in FIG. 3) so that rod 16 can be threadably engaged therewith. In such a case, an adjustment nut 20 can be coupled to an opposing outboard end 162 of rod 160 so that the axial position of rod 16 in housing 14 can be adjusted. When connector 10 is assembled as shown in FIG. 4, longitudinal axis 125 of bore 124 is aligned with longitudinal axis 145 of bore 144.

Rod 16 includes (e.g., integrated therewith, attached thereto, etc.) a central region thereof that defines a machine taper 164 (e.g., a Jacobs taper) that moves in correspondence with movement of rod 16. More specifically, machine taper 164 is designed to engage machine taper tunnel region 124A when handle 18 is in the down/locked position as shown. That is, in this position, housings 12/14 are drawn toward one another by rod 16 such that taper 164 "locks" into taper tunnel region 124A thereby preventing housing 12 from swiveling (relative to housing 14) about rod 16. Note that the locked position of handle 18 simultaneously causes S/T tunnel regions 120/140 to approximate a taper tunnel (e.g., a machine taper tunnel such as a Jacobs taper tunnel) as the corresponding widths of slots 122/142 is decreased to the point that slots 122/142 close up or nearly close up as housings 12/14 are drawn toward one another. (For clarity of illustration, the widths of slots 122/142 in the illustrated locked position have been exaggerated.) The resulting size of the approximated taper tunnels caused by the closing (or near closing) of slots 122/142 is selected to cooperate with a taper rod/pin (not shown) inserted in each of the so-approximated taper tunnels such that each S/T tunnel region locks onto its engaged rod/pin. Each such inserted taper rod/pin would generally be coupled to another fixture, mechanism, etc. (not shown) that is to be connected to connector 10.

When handle 18 is pivoted away from housing 12/14 (as indicated by arrow 100) to a release or unlocked position, housings 12/14 are pushed away from one another by rod 16 such that machine taper 164 disengages just enough from machine taper tunnel region 124A to permit housing 12 to swivel about the longitudinal axis of rod 16 relative to housing 14. Additional features can be coupled to one or more of housing 12, housing 14, and/or rod 16 to assist the disengagement of machine taper 164 from machine taper tunnel region 124A without departing from the scope of the present invention. Note that the unlocked position of handle 18 simultaneously causes the widths of slots 122/142 to increase or open up such that S/T tunnel regions 120/140 relax their engagement with the corresponding rod/pin inserted therein. That is, the unlocked position of handle 18 allows connector 10 to swivel about each engaged rod/pin and any elements/fixtures/mechanisms connected thereto at S/T tunnel regions 120/140, while simultaneously allowing housing 12 to swivel relative to housing 14 about rod 16.

Another embodiment of the present invention is illustrated in FIG. 5 where common reference numerals are used for features of previously-described connector 10. In addition, FIG. 5 illustrates a protective sleeve 30 provided over the adjacent portions of housings 12 and 14 in order to keep dust/dirt from entering the housings' bores. Protective sleeve 30 could be integrated with housing 12 or housing 14 without departing from the scope of the present invention.

The advantages of the present invention are numerous. The swiveling taper lock connector essentially provides an unlimited number of positions and orientations. A single lock/unlock handle provides for both one-handed manipulation of the connector and one-handed locking of the connector in a desired position for greatest efficiency.

Although the invention has been described relative to specific embodiments thereof, there are numerous variations and modifications that will be readily apparent to those skilled in the art in light of the above teachings. For example, the machine taper tunnel region (i.e., region 124A in connector 10) can be machined into a separate element that is then threaded into housing 12 as shown in FIG. 6. More specifically, a sleeve element 200 is externally threaded for engagement with housing 12 to thereby define a machine taper tunnel 200A (e.g., a Jacobs taper tunnel). It is therefore to be understood that, within the scope of the appended claims, the invention may be practiced other than as specifically described.

What is claimed as new and desired to be secured by Letters Patent of the United States is:

1. A connector, comprising:
   a first housing having a first bore hole longitudinally extending through said first housing and terminating in a machine taper tunnel, a first tapered hole transversely extending through said first housing for receiving a bar of one of a surgical head clamp and a mounting frame of an operating table, and a first slot extending through said first housing across said first bore hole to said first tapered hole;
   a second housing having a second bore hole longitudinally extending through said second housing, a second tapered hole transversely extending through said second housing for receiving a bar of the other of the surgical head clamp and the mounting frame of an operating table, and a second slot extending through said second housing across said second bore hole to said second tapered hole;
   a rod disposed in said first bore hole and said second bore hole, said rod extending across said first slot and said second slot, said rod terminating at a first end and a second end, said second end being coupled to said second housing, said rod having a machine taper coupled thereto between said first end and said second end for engagement with said machine taper tunnel;

a sleeve disposed circumferentially around a cylindrical portion of said first housing and a cylindrical portion of said second housing for preventing contaminants from entering said first bore hole and said second bore hole; and a lever pivotally coupled to said first end of said rod, wherein a pivoting movement of said lever clamps a cam of said lever against said first housing and simultaneously causes said machine taper to move relative to and clamp against said machine taper tunnel, a change in width of said first slot, and a change in width of said second slot.

2. A connector as in claim 1, wherein a longitudinal axis of said first bore hole is approximately perpendicular to a longitudinal axis of said first tapered hole.

3. A connector as in claim 1, wherein a longitudinal axis of said second bore hole is approximately perpendicular to a longitudinal axis of said second tapered hole.

4. A connector as in claim 1, wherein a longitudinal axis of said first bore hole is approximately perpendicular to a longitudinal axis of said first tapered hole, and wherein a longitudinal axis of said second bore hole is approximately perpendicular to a longitudinal axis of said second tapered hole.

5. A connector as in claim 1, wherein said machine taper tunnel and said machine taper comprise a Jacobs taper.

6. A connector, comprising:
a first housing having a first bore hole longitudinally extending through said first housing and terminating in a machine taper tunnel, a first tapered hole transversely extending through said first housing for receiving a bar of one of a surgical head clamp and a mounting frame of an operating table, and a first slot extending through said first housing across said first bore hole to said first tapered hole;

said first bore hole having a first longitudinal axis;

a second housing having a second bore hole longitudinally extending through said second housing, a second tapered hole transversely extending through said second housing for receiving a bar of the other of the surgical head clamp and the mounting frame of an operating table, and a second slot extending through said second housing across said second bore hole to said second tapered hole;

said second bore hole having a second longitudinal axis;

a rod disposed in said first bore hole and said second bore hole wherein said first longitudinal axis is aligned with said second longitudinal axis, said rod extending across said first slot and said second slot, said rod terminating at a first end and a second end, said second end being rigidly coupled to said second housing, said rod having a machine taper coupled thereto between said first end and said second end for engagement with said machine taper tunnel in said first housing;

a sleeve disposed circumferentially around a cylindrical portion of said first housing and a cylindrical portion of said second housing for preventing contaminants from entering said first bore hole and said second bore hole, said sleeve being integrated with one of said first housing and said second housing; and a lever pivotally coupled to said first end of said rod, wherein a pivoting movement of said lever clamps a cam of said lever against said first housing and causes said machine taper to move relative to and clamp against said machine taper tunnel, and said first and second slots to contract.

7. A connector as in claim 6, wherein said longitudinal axis of said first bore hole is approximately perpendicular to a longitudinal axis of said first tapered hole.

8. A connector as in claim 6, wherein said longitudinal axis of said second bore hole is approximately perpendicular to a longitudinal axis of said second tapered hole.

9. A connector as in claim 6, wherein said longitudinal axis of said first bore hole is approximately perpendicular to a longitudinal axis of said first tapered hole, and wherein said longitudinal axis of said second bore hole is approximately perpendicular to a longitudinal axis of said second tapered hole.

10. A connector as in claim 6, wherein said machine taper tunnel and said machine taper comprise a Jacobs taper.

11. A connector, comprising:
a first housing having a first bore hole longitudinally extending through said first housing and terminating in a machine taper tunnel, a first tapered hole transversely extending through said first housing for receiving a bar of one of a surgical head clamp and a mounting frame of an operating table, and a first slot extending through said first housing across said first bore hole to said first tapered hole;

said first bore hole having a first longitudinal axis;

a second housing having a second bore hole longitudinally extending through said second housing, a second tapered hole transversely extending through said second housing for receiving a bar of the other of the surgical head clamp and the mounting frame of an operating table, and a second slot extending through said second housing across said second bore hole to said second tapered hole;

said second bore hole having a second longitudinal axis;

a rod disposed in said first bore hole and said second bore hole wherein said first longitudinal axis is aligned with said second longitudinal axis, said rod extending across said first slot and said second slot, said rod terminating at a first end after said rod crosses said first slot, said rod terminating in a second end after said rod crosses said second slot, said second end being rigidly coupled to said second housing, said rod having a machine taper coupled thereto between said first end and said second end for engagement with said machine taper tunnel in said first housing;

a sleeve disposed circumferentially around a cylindrical portion of said first housing and a cylindrical portion of said second housing for preventing contaminants from entering said first bore hole and said second bore hole, said sleeve being integrated with one of said first housing and said second housing; and a lever pivotally coupled to said first end of said rod, wherein a pivoting movement of said lever clamps a cam of said lever against said first housing and causes said machine taper to move relative to and clamp against said machine taper tunnel, and said first and second slots to contract.

12. A connector as in claim 11, wherein said longitudinal axis of said first bore hole is approximately perpendicular to a longitudinal axis of said first tapered hole.

13. A connector as in claim 11, wherein said longitudinal axis of said second bore hole is approximately perpendicular to a longitudinal axis of said second tapered hole.

14. A connector as in claim 11, wherein said longitudinal axis of said first bore hole is approximately perpendicular to a longitudinal axis of said first tapered hole, and wherein said longitudinal axis of said second bore hole is approximately perpendicular to a longitudinal axis of said second tapered hole.

15. A connector as in claim 11, wherein said machine taper tunnel and said machine taper comprise a Jacobs taper.

* * * * *